Figure 1:
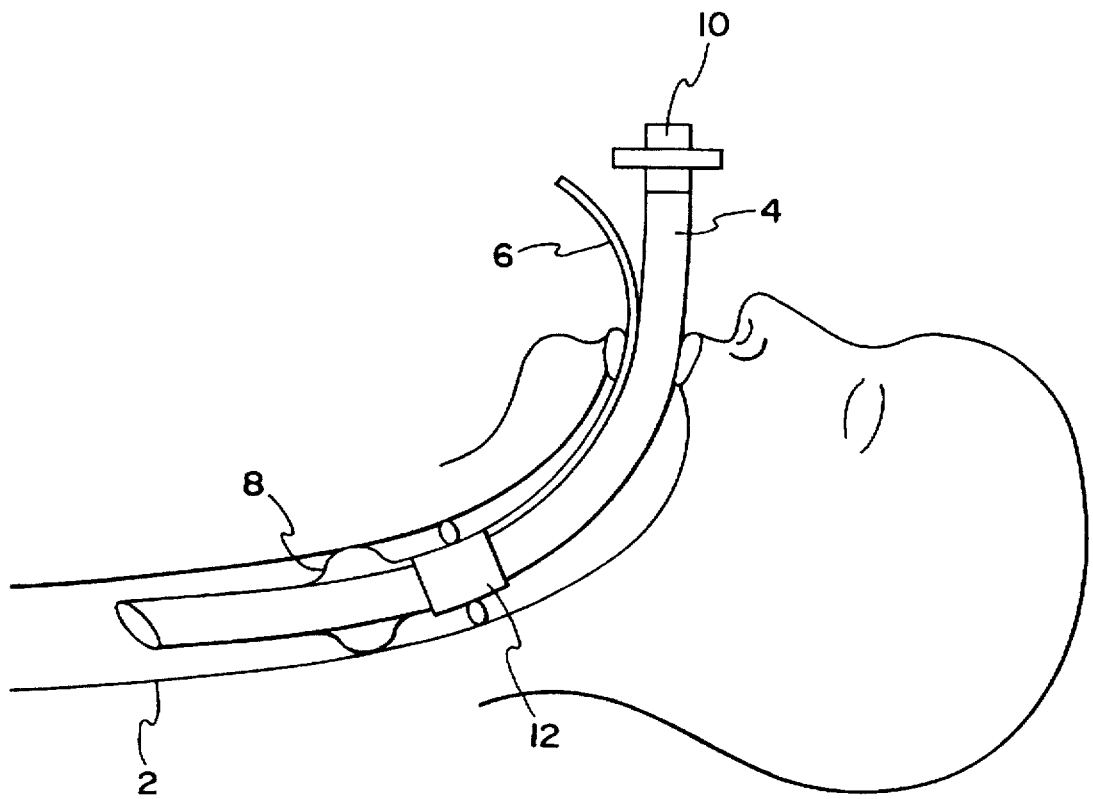

United States Patent [19]

Hartmann et al.

[11] Patent Number: 5,725,510
[45] Date of Patent: Mar. 10, 1998

[54] ENDOTRACHEAL TUBE

[76] Inventors: Michael Hartmann, Möslestrasse 12, D-79232 March, Breisgau, Germany; Bert Müller, Rue des Alpes 6 A, CH-1020 Renens, Switzerland

[21] Appl. No.: 545,570
[22] PCT Filed: May 19, 1994
[86] PCT No.: PCT/EP94/01621
§ 371 Date: Feb. 21, 1996
§ 102(e) Date: Feb. 21, 1996
[87] PCT Pub. No.: WO94/27652
PCT Pub. Date: Dec. 8, 1994

[30] Foreign Application Priority Data

May 20, 1993 [DE] Germany .............. 43 16 920.1

[51] Int. Cl.⁶ .................................................. A61M 5/00
[52] U.S. Cl. ............................................................. 604/265
[58] Field of Search ........................... 604/265, 264, 604/285, 266, 272, 275

[56] References Cited

U.S. PATENT DOCUMENTS

| | | |
|---|---|---|
| 3,610,247 | 10/1971 | Jackson . |
| 3,902,500 | 9/1975 | Dryden . |
| 4,054,139 | 10/1977 | Crossley . |
| 4,581,028 | 4/1986 | Fox, Jr. et al. . |
| 4,603,152 | 7/1986 | Laurin et al. . |
| 4,612,337 | 9/1986 | Fox, Jr. et al. . |

FOREIGN PATENT DOCUMENTS

| | | |
|---|---|---|
| 0 558 588 | 2/1987 | Australia . |
| 0 206 024 | 6/1986 | European Pat. Off. . |
| 0 302 186 | 5/1988 | European Pat. Off. . |
| 0 301 717 | 7/1988 | European Pat. Off. . |
| 0 318 258 | 11/1988 | European Pat. Off. . |
| 2.109.932 | 9/1971 | France . |
| 3302567 A1 | 1/1983 | Germany . |
| 32 28 849A1 | 2/1984 | Germany . |
| 89 15 538.6 U | 7/1989 | Germany . |
| 3300203 C2 | 12/1990 | Germany . |
| 39 42 112A1 | 6/1991 | Germany . |
| 41 15 390A1 | 4/1992 | Germany . |
| 43 16 920.1 | 10/1993 | Germany . |

Primary Examiner—John D. Yasko
Attorney, Agent, or Firm—Shlesinger, Arkwright & Garvey, LLP

[57] ABSTRACT

The invention concerns an endotracheal tube with a collar. In order to avoid as far as possible the danger of a pulmonary infection caused by microbes introduced along the tube, at least one device with an antimicrobial action is fitted at one or more points (12) on the outer surface of the tube. This device consists preferably of a piece of silver foil, vapor-deposited silver or a silver compound (silver salt), or may also be a length of tubing fitted in the tube.

5 Claims, 1 Drawing Sheet

ENDOTRACHEAL TUBE

The invention concerns au endotracheal tube defined in the preamble of claim 1.

There is danger of pneumonia when using artificial respiration on account of germs carried along the tube into the lungs.

The object of the present invention is therefore to so design an endotracheal tube that the danger of pneumonia caused by germs carried along the tube is extensively avoided.

This problem is solved by the design characterized in claim 1.

Advantageous and appropriate other developments of the invention are stated in the sub-claims.

The design of the invention fits the endotracheal tube with a germ-barrier. The invention's design is based on the known insight that certain substances such as silver and silver salts already in trace form are highly bactericidal and bacteriostatic. Regarding silver and silver salts, such effects are provided by the silver ions. Because of the deposition of an antimicrobial agent proposed by the invention, for instance silver or silver salts, onto one or more circumferential sites of the tube, or by the insertion of a correspondingly designed tubular stub, antimicrobial substances, for instance antimicrobial silver ions, are produced automatically, and thereby an antimicrobial region is created round the tube and prevents the germs from penetrating this tube and thus the lungs.

The invention is elucidated below in relation to the drawing showing an illustrative embodiment.

The drawing schematically shows an endotracheal tube 4 inserted into the human windpipe 2 and fitted with a blocking cuff 8 which is inflatable through a hose 6, said tube comprising a fitting 10 at its outer end for an omitted respiration hose.

An antimicrobial agent for instance in the form of a silver foil, a coating of silver or of a silver-salt is present at the periphery of the tube 4 at a site before the blocking cuff 8. The silver coating may be deposited by evaporation. Such an antimicrobial agent may be present at several sites on the tube.

In the embodiment shown, the antimicrobial site is located directly before the blocking cuff 8 in the zone of the glottises 14.

Alternatively the outside of the blocking cuff 8 may comprise the deposited antimicrobial agent 12, that is the silver foil, a coating of silver or of a silver-salt.

The antimicrobial agent 12 also may be a tubular stub inserted into the tube and composed of silver, or being silvered, or being the substrate of an antimicrobial substance such as a silver salt.

The silver or the silver salt produce an antimicrobial endotracheal tube. Saliva always collecting between the tube and the windpipe, hence silver or silver salt being constantly enclosed in a liquid medium, silver atoms, which are known to be antimicrobial, automatically will go into solution.

It is furthermore possible to dissolve silver ions from the silver foil or the evaporated silver coating or the tubular stub by applying a DC voltage, in which case the silver or the tubular stub will act as the dissolving electrode (anode).

We claim:

1. An endotracheal tube comprising:

a) an elongated tubular member having a first end and a second end;

b) at least one blocking cuff positioned along the outer surface of said tubular member for forming a seal against the trachea of a patient and between said first and second ends; and c) said outer surface of said tubular member provided with an antimicrobial agent disposed adjacent said at least one blocking cuff, said antimicrobial agent is selected from the group consisting of silver evaporation deposit, silver salt coating and metal foil, said foil further comprising at least one of silver, a silver evaporate coating and a silver salt coating whereby during use said antimicrobial agent is caused to release metal ions into the fluid medium collecting about said at least one cuff to provide an antimicrobial barrier around said tube for preventing the passage of germs therearound.

2. An endotracheal tube as in claim 1 and wherein:

a) said metal foil is an anode powered by DC.

3. An endotracheal tube as in claim 1 and wherein:

a) one of said ends is adapted to be fitted to a respiration hose and said antimicrobial agent is positioned between said cuff and said respiration hose adapted end.

4. An endotracheal tube as in claim 1 and wherein:

a) said antimicrobial agent forming at least part of said at least one blocking cuff.

5. An endotracheal tube as in claim 1 and wherein:

a) said antimicrobial agent is positioned along additional regions of said outer surface of said tubular member.

* * * * *